US006403853B1

(12) United States Patent
Abrevaya et al.

(10) Patent No.: US 6,403,853 B1
(45) Date of Patent: Jun. 11, 2002

(54) OLEFIN OLIGOMERIZATION USING SURFACE MODIFIED MOLECULAR SIEVE CATALYST

(75) Inventors: Hayim Abrevaya, Wilmette; Robert R. Frame, Glenview, both of IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 09/667,167

(22) Filed: Sep. 21, 2000

(51) Int. Cl.$^7$ ............................ C07C 2/24; C07C 2/02
(52) U.S. Cl. ..................... 585/533; 585/514; 585/531
(58) Field of Search ........................... 585/514, 531, 585/533; 502/85

(56) References Cited

U.S. PATENT DOCUMENTS

| | | | |
|---|---|---|---|
| 3,981,941 A | 9/1976 | Butter | 260/683.15 D |
| 4,520,221 A | 5/1985 | Hsia Chen | 585/517 |
| 4,547,613 A | 10/1985 | Garwood et al. | 585/533 |
| 4,642,404 A | 2/1987 | Shihabi | 585/415 |
| 4,902,847 A | 2/1990 | Juguin et al. | 585/533 |
| 5,182,242 A | * 1/1993 | Marler | 502/66 |
| 5,284,989 A | 2/1994 | Apelain et al. | 585/533 |
| 5,292,990 A | 3/1994 | Kantner et al. | 585/820 |
| 5,506,182 A | 4/1996 | Yamagishi et al. | 503/66 |
| 5,895,830 A | 4/1999 | Stine et al. | 585/259 |

FOREIGN PATENT DOCUMENTS

WO  WO 97/04871  2/1997

* cited by examiner

*Primary Examiner*—Thuan D. Dang
(74) *Attorney, Agent, or Firm*—John G. Tolomei; Frank S. Molinaro; Maryann Maas

(57) ABSTRACT

In a process for the oligomerization of light olefins (e.g. propylene) to more valuable higher olefins (e.g. hexene), the use of a molecular sieve (e.g. SAPO-11) that has been acid washed has shown to provide superior selectivity to, and yield of, the desired product. These benefits are attributed to a reduction in non-selective acid sites as well as an increase in phosphorous content (in the case of SAPO molecular sieves) at the molecular sieve crystallite surface, a probable result of removing amorphous silicon aluminum phosphate acid, silicophosphorous acids, and/or phosphoric acids. Furthermore, this removal is likely accompanied by an increased accessibility of olefinic feed components to the so-called "selective" acid sites within the sieve pores. Post-synthesis acid washing of the molecular sieve has not only demonstrated a narrower carbon number distribution of olefin oligomers, but also improved the linearity of the oligomerized olefinic product slate in general. Such increases in linearity generally correspond to overall higher product values, when downstream applications such as plasticizer intermediates are considered.

12 Claims, No Drawings

OLEFIN OLIGOMERIZATION USING SURFACE MODIFIED MOLECULAR SIEVE CATALYST

FIELD OF THE INVENTION

The present invention relates to a process for the oligomerization of olefins (e.g. propylene) to higher value products (e.g. hexene) using a molecular sieve catalyst. In such a process, acid washing of the molecular sieve prior to use results in increased selectivity of the oligomerization reaction to the desired product.

BACKGROUND OF THE INVENTION

Processes for the oligomerization of light olefins (e.g. ethylene, propylene, and butylene) to produce higher carbon number olefin products (e.g. $C_6^+$ olefins) are well known. Oligomerization processes have been employed to produce high quality motor fuel components as well as petrochemicals from ethylene, propylene, and butylene. These oligomerization processes are also referred to as catalytic condensation and polymerization, with the resulting motor fuel often referred to as polymer gasoline. In the refining area, methods have been continually sought to improve the octane number of the gasoline boiling range oligomerization products. This octane enhancement is generally realized through the improvement of the oligomerization reaction selectivity to enhance the representation of high octane blending components (e.g. branched olefins) in the product slate. The ability of the process to better target specific carbon number species is also a primary consideration when highly purified chemical grade products are desired. In any case, the enrichment of product slate to the targeted species, in addition to providing a higher quality and quantity of useable products, also benefits catalyst life. This is due to the reduction in non-selective heavy oligomers that condense into coke which ultimately covers the catalyst.

Known catalysts for effecting the oligomerization reaction include heterogeneous catalysts such as solid acids and homogeneous catalysts, in particular boron trifluoride as described, for example, in U.S. Patent No. 3,981,941. Other catalysts fall within the description of mild protonic acids, generally having a Hammett acidity function of less than −5.0. Particularly preferred among these are solid phosphoric acid (SPA) catalysts having as a principal ingredient an acid of phosphorous such as ortho, pyro, or tetraphosphoric acid. Details of SPA catalysts are provided in the prior art, for example in U.S. Pat. No. 5,895,830.

The use of zeolites, particularly those of the medium pore consideration, as oligomerization catalysts is also described, along with various catalyst treatment methods designed to improve performance. U.S. Pat. No. 4,547,613 discloses the use of a ZSM-5 type catalyst that has been conditioned by treatment with a light hydrocarbon gas at low pressure and elevated temperature. U.S. Pat. No. 4,520,221 describes a process for providing high yields of lubricating oils from the conversion of light olefins such as propylene using ZSM-5 catalyst. The results are achieved through removing the surface acidity of the catalyst by treatment with a bulky amine. U.S. Pat. No. 4,642,404 is directed to the conversion of $C_2^+$ olefins to $C_5^+$ olefins over a catalyst of a bound, high silica zeolite having a constraint index of 1–12. The catalyst is modified, while it is at least partially in the hydrogen form, by steaming to improve activity.

Finally, U.S. Pat. No. 5,284,989 discusses the use of a constrained intermediate pore siliceous acidic zeolite (e.g. ZSM-22, -23, or -35) having Brönsted acid activity and wherein the zeolite surface is rendered substantially inactive for acidic reactions. The zeolite can be inactivated by contact with dicarboxylic acid (e.g. oxalic acid). The reference states that treatments with strong acids such as HCl, $HNO_3$, and $H_2SO_4$ "are limited, in many cases, . . . by the onset of crystal degradation and loss of sorption capacity."

In contrast to the prior art, and specifically the teachings of the '989 patent, the present invention is based on the realization that treatment of solid oligomerization catalysts with a strong acid provides significant benefits in terms of product selectivity and yield. The unexpected improvements in process performance associated with the present invention are believed to directly result from changes in catalyst surface properties stemming from the acid treatment.

SUMMARY OF THE INVENTION

In a broad embodiment the present invention is a process for oligomerizing an olefinic feed, the process, comprising:

a) providing a catalyst comprising a crystalline silicoaluminate or metalloaluminophosphate molecular sieve characterized by a 3-dimensional framework structure and having a chemical composition on an anhydrous basis expressed by an empirical formula of:

$$(EL_xAl_yP_z)O_2$$

where EL is an element selected from the group consisting of silicon, magnesium, zinc, iron, cobalt, nickel, manganese, chromium and mixtures thereof; "x" is the mole fraction of EL and has a value of at least 0.005; "y" is the mole fraction of Al and has a value of at least 0.01; "z" is the mole fraction of P and has a value from 0 to about 0.6; EL is silicon when z=0; and x+y+z=1, the molecular sieve having been washed at washing conditions with a strong acid having a $pK_a$ of less than about 2.0, and;

b) contacting the light olefin feed with the catalyst at oligomerization conditions to yield a higher olefin product.

In a more specific embodiment the present invention is as described above, where the light olefin feed comprises propylene, the catalyst is a silicon aluminophosphate having the crystal structure of SAPO-11, and the higher olefin product comprises hexene present in an amount of at least 30% by weight, relative to the light olefin feed weight.

DETAILED DESCRIPTION OF THE INVENTION

The feed for the process of the present invention generally comprises light olefin components, typically $C_2$ to $C_5$ olefins, although olefins with higher carbon numbers may also be used. Sources of the olefin feeds normally include: light gas streams recovered from the gas separation section of a refinery fluid catalytic cracking (FCC) process, $C_4$ streams from steam cracking and coker off gas, or the effluents from light paraffin (e.g. LPG) dehydrogenation zones. In most operations, the combined $C_3$ and $C_4$ olefins will account for at least 50% by weight of the total feed olefins. Certain situations may also warrant the oligomerization of feeds having, with respect to their olefin content, exclusively ethylene, propylene, or butylene (either pure isomers or mixed normal and branched isomers) to obtain relatively high yields of a given carbon number product. If a feed comprising predominantly propylene (or predominantly propylene with an inert diluent such as propane) is processed, the dimer (hexene) and trimer (nonene) are generally the desired products and their yields can be maximized using the acid-washed molecular sieve catalyst of the present invention, combined with optimizing the reaction conditions. Likewise, a butylene feed may be incorporated to target primarily an octene product or a product containing octenes as well as dodecenes.

The acid-washed molecular sieve provides exceptional results for both liquid- and gas-phase operation, although maintaining the feed in the liquid phase is generally preferred. Furthermore, it is certainly within the scope of the present invention to combine the feed with a number of diluents known in the art, such as heavy paraffins. The use of these additives, as described in U.S. Pat. Nos. 6,080,903; 6,072,093; 5,990,367; and 5,895,830, provides a number of benefits including catalyst performance enhancement and promotion of liquid-phase conditions in the reaction zone.

The catalyst comprises a molecular sieve, which refers to a broad class of crystalline materials understood in the art to include both aluminosilicates (i.e. zeolites) and metalloaluminophosphates (e.g. SAPOs). While a zeolite is a crystalline aluminosilicate, a metalloaluminophosphate contains phosphorous cations ($P^{+5}$) in addition to aluminum ($Al^{+3}$) and silicon ($Si^{+4}$) situated within tetrahedral sites of an extensive three-dimensional network of oxygen ions. Types of materials classified as molecular sieves are explained in detail in *Molecular Sieves, Principles of Synthesis and Identification* by R. Szostak (Van Nostrand Reinhold, 1989) at pages 2–4. These include silicas, metalloaluminates, aluminophosphates, and others.

In focusing on the zeolite and metalloaluminophosphate molecular sieves found to be useful in the oligomerization process of the present invention, the range of suitable materials is encompassed by those having a three-dimensional microporous framework structure having the empirical formula:

$$(EL_xAL_yP_z)O_2$$

where EL is an element selected from the group consisting of silicon, magnesium, zinc, iron, cobalt, nickel, manganese, chromium and mixtures thereof, "x" is the mole fraction of EL and has a value of at least 0.005, "y" is the mole fraction of Al and has a value of at least 0.01, "z" is the mole fraction of P and has a value from 0 to about 0.6. In all cases, $x+y+z=1$. In the specific case where $z=0$, EL is necessarily silicon and the molecular sieve is a zeolite material, or a crystalline aluminosilicate. When EL is a mixture of elements, "x" represents the total amount of the element mixture present. The molecular sieve therefore contains tetrahedral units of $AlO_2$ and $ELO_2$ (as well as units of $PO_2$ when $z>0$) in its framework structure. Preferred elements (EL) are silicon, magnesium and cobalt with silicon being especially preferred.

The preparation of these various "ELAPO" molecular sieve materials as defined above is well known in the art and may be found in U.S. Pat. Nos.: 4,554,143 (FeAPO); 4,440,871 (SAPO); 4,853,197 (MAPO, MnAPO, ZnAPO, CoAPO); 4,793,984 (CAPO), 4,752,651 and 4,310,440, all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the salts of the EL element such as the chloride and nitrate salts. When EL is silicon a preferred source is fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH).

After the initial synthesis, the ELAPOs will usually contain some of the organic templating agent in its pores. In order for the ELAPOs to be active catalysts, the templating agent in the pores must be removed by heating the ELAPO powder in an oxygen-containing atmosphere at a temperature of about 200° to about 700° C. until the template is removed, usually a few hours.

A preferred embodiment of the invention is one in which the element (EL) content of the ELAPO molecular sieve varies from about 0.005 to about 0.05 mole fraction. If EL is more than one element, then the total concentration of all the elements is between about 0.005 and 0.05 mole fraction. An especially preferred embodiment is one in which EL is silicon (usually referred to as SAPO). The SAPOs that can be used in the present invention are any of those described in U.S. Pat. Nos. 4,440,871; 5,126,308; and 5,191,141. SAPO catalysts that are suitable for the present invention include SAPO-11 and SAPO-41. Of the specific crystallographic structures described in the '871 patent, the SAPO-11, i.e., structure type 11, is preferred. The SAPO-11 structure is characterized in that it has elliptically shaped pores with an average diameter of about 5.1 Å. In this case, the average pore opening is defined as the average length of the major and minor axes across the elliptically shaped pore formed by a 10-membered ring structure. In terms of the kinetic diameters of molecules, SAPO-11 adsorbs cyclohexane (kinetic diameter of 6.0 Å) but does not adsorb neopentane (kinetic diameter of 6.2 Å) to a significant extent. Another SAPO, SAPO-41, as exemplified in Example 54 of the '871 patent, is also preferred. The SAPO-41 structure is also characterized in that it adsorbs cyclohexane but not neopentane.

An important feature that characterizes the preferred SAPO-11 and SAPO-41 materials described above is their "intermediate" pore diameters. In determining the appropriate pore size for a given application, the Pore Size Index, or value of the product of the two major axes (in angstroms) of the crystallite pores is a useful measure. Values of the Pore Size Index of various crystalline materials are provided in the "Atlas of Zeolite Structure Types" by W. M. Meier and D. H. Olson, Butterworths, publisher, Third Revised Edition, 1992. For purposes of the present invention, the molecular sieve will preferably have a Pore Size Index in the Range from about 20 to about 40. In general, this range of crystallite pore size is desirable for the oligomerization of light olefins, because the proper selectivity is provided for reacting specifically shaped and sized molecules, as dictated by the configuration of the microporous channels through which they must diffuse. In the case of the process of the present invention, the above range of pore sizes has been determined to provide shape-selectivity to the highly valued $C_6$–$C_9$ olefinic products by allowing passage of both linear feed and product molecules, while rejecting highly branched and ring structures and molecules of high molecular weight (e.g. $C_{12}^+$ olefins).

The proper pore size is most often found in zeolites and SAPOs having micropores defined by 10-membered ring structures, as opposed to those molecular sieves with frameworks characterized by either 8- or 12-membered rings. Appropriately, therefore, the aforementioned SAPO-11 and SAPO-41 are both examples of 10-membered ring structures. The 10-membered zeolites or aluminosilicates preferable for use in the present invention include ZSM-5, defined in U.S. Pat. No. 3,702,886, incorporated by reference; ZSM-11, defined in U.S. Pat. No. 3,709,979, incorporated by reference; ZSM-22, defined in European Pat. No. 102716, incorporated by reference, ZSM-23, defined in U.S. Pat. No. 4,076,842, incorporated by reference; ZSM-35, defined in U.S. Pat. No. 4,016,245, incorporated by reference; some of the silicalite materials, defined in U.S. Pat. No. 4,061,724, incorporated by reference; and ferrierite, defined in U.S. Pat. No. 3,933,974, incorporated by reference. A further method of classifying the pore size openings of the zeolites and SAPO materials preferred in the present invention is the "Constraint Index" (CI). This term is defined specifically for 10-membered ring structures by J. Weitkamp (*Host/Guest Chemistry and Catalysis in Zeolites*, proceedings at the 9$^{th}$ International Zeolite Conference, Montreal 1992, edited by R. von Ballmoos et al., 1993 by Butterworth-Heinemann) according to the relative uptake of the n-decane isomerization products, 2-methylnonane and 5-methylnonane. For purposes of the present invention, the molecular sieve catalyst will have a CI preferably in the range from about 5 to about 14.

An essential feature of the oligomerization process of the present invention is associated with the realization that the molecular sieve catalyst exhibits substantially improved performance after it has been acid washed with a strong acid. By strong acid is meant one having a $pK_a$ value of less than about 2, and preferably less than about 0, where $pK_a$ is understood in the art to be defined as $-\log K_a$, and $K_a$ is the equilibrium dissociation constant of the acid in water. Acids that may be used therefore include, but are not limited to, aqueous solutions of $HNO_3$, HCl, HBr, HI, $H_2SO_4$, and mixtures thereof. A preferred acid is $HNO_3$. The acid concentration used in the washing procedure, as outlined in detail hereinafter, depends on the stability of the particular molecular sieve employed. In general, degradation of the crystallite structure is substantially avoided when the acid solution has a pH value from about 1 to about 4. A simple test to determine whether a specific acid molecular sieve combination is suitable comprises subjecting a sample of the molecular sieve to the acid solution under acid washing conditions for a period of 24 hours. Any substantial dissolution of the molecular sieve framework appears as a cloudy precipitate in the liquid.

The acid washing procedure comprises contacting the molecular sieve crystallites with any of the aforementioned acids in either a batch or continuous mode. Preferably, the molecular sieve is maintained in a bed over which aqueous acid solution is circulated for a specified residence time. In this continuous washing process, it is usually desirable to add sufficient concentrated acid (e.g. a 20 wt-% $HNO_3$ stock solution) to maintain a pH within the preferred range from about 1 to about 4. An equivalent amount of solution (based on the water content of the added acid) may then be withdrawn from the system. Of course, recirculation of the acid wash solution is not essential, and it is also possible to simply pass the acid solution, once through, over a bed of the molecular sieve. This type of operation, however, tends to result in either discarding an unnecessary amount of acid at high flow rates or achieving sub-optimal liquid/solid contact at low flow rates. At the other extreme, batch-wise acid washing is also possible, but some make-up acid addition may still be required to maintain the proper pH.

Regardless of the use of either batch or continuous washing, the residence, or contact, time between the acid and the molecular sieve, as calculated according to methods well known in the art, is preferably from about 0.5 to about 48 hours, and more preferably from about 1 to about 24 hours. Pressure is not a critical variable for the acid washing, and ambient pressure is generally chosen for convenience. The temperature used is preferably from about 0° C. to about 100° C., where higher temperatures generally expedite the acid washing effects at the expense of increased corrosivity of the acid to the molecular sieve structure. While the acid washing is generally employed after formation of the molecular sieve crystallites, it is also possible to achieve the desired catalytic performance benefits even when acid washing is saved until after an optional binding step, where the molecular sieve is bound into larger particles suitable for commercial applications. In this case, the stability of the binder in the acid solution must be considered.

After completion of the acid wash, the molecular sieve is then typically filtered to separate any fine particles dislodged in the washing step and thereafter flushed with water until the effluent pH is at least 5. The resulting acid-washed molecular sieve is then dried with or without the application of heat. Multiple washings may be employed to achieve the desired final catalyst properties. The washing may also be preceded or followed by steaming that is sometimes used to de-aluminate the molecular sieve.

In a light olefin oligomerization process, the performance benefit of using a catalyst comprising the acid-washed molecular sieve is quantified in terms of increased selectivity in the reaction product slate to desired species. Surprisingly, this selectivity benefit does not come at the expense of reduced olefin conversion, as is normally the case for conventional non acid-washed molecular sieves. Rather, acid-washed materials can be used to achieve substantially improved selectivity to a desired species (e.g. hexene), where this selectivity enhancement corresponds to an increase, rather than a decrease, in conversion (e.g. an increase from 85% to 90% conversion). Thus, the overall yield of desired product is markedly improved using the simple acid washing technique of the present invention.

The use of an acid-washed catalyst comprising SAPO-11, for example, provides a product slate, compared to that obtained using non acid-washed material, that is greatly enriched in propylene dimer and trimer, but depleted of the less-valuable tetramer. The dimer (hexene) and trimer (nonene) are known to be valuable intermediates for co-monomer and for platicizer production, respectively. Furthermore, the selectivity of the acid-washed molecular sieve catalyst can favor propylene dimer production to an extent unrealized with conventional oligomerization catalysts, including those comprising zeolites and solid phosphoric acid (SPA) catalysts. In a preferred embodiment, when the feed stock excluding any diluents comprises substantially pure $C_3$ olefins, the hexene present in the product stream (i.e. hexene yield) will account for at least 20% by weight, and more preferably at least 30% by weight, of the feed olefins processed. The acid-washed molecular sieve catalyst likewise shows a significant benefit in terms of activity and product selectivity for the oligomerization of $C_4$ olefins to their corresponding dimers and trimers.

An additional benefit of the acid treatment or wash, which will become more apparent from the following explanation regarding the improvement in catalyst shape selectivity, is a smaller degree of branching (i.e. a greater degree of linearity) achieved for the entire product slate of oligomers produced. For example, the oligomerization of propylene is accompanied to some extent, through cracking and rearrangement, by the co-production of heptene. Again using the specific comparative data for propylene oligomerization over art acid-washed and non-acid washed SAPO-11, the linear and mono-branched $C_7$ olefin byproduct as a fraction of the total heptene produced is significantly greater for the acid-washed material. Preferably, therefore, using the catalyst of the present invention and a feed comprising propylene, the combined contribution of linear heptene and methyl hexenes (i.e. 2-methyl-hexene and 3-methyl-hexene) to the total $C_7$ olefin byproduct is at least 40%, and more preferably at least 50% by weight. As is known in the art, the value of the $C_7$ olefin byproduct for its main downstream commercial uses as either a plasticizer or a precursor for linear alkylbenzene (LAB) production is determined primarily from its degree of branching. Therefore, the reduction in more highly branched $C_7$ species (i.e. dimethyl pentenes) resulting from the acid wash is a further important advantage associated with the present invention. Correspondingly, major oligomerization products, for example hexene and nonene, are similarly less branched and consequently more valuable intermediates.

Without limiting the scope of the invention according to any particular theory, a mechanism by which the previously unrecognized and significant benefits of acid washed molecular sieves in oligomerization processes is proposed. Namely, it is thought that acid washing influences access of the feed components to the molecular sieve by removing debris remaining from the synthesis thereof. Possibly, this debris itself, similar to the molecular sieve, has acidic properties capable of catalyzing oligomerization reactions. Thus, the removal of this material can provide the beneficial result of removing non-selective acid sites, unlike those within the pores of the crystalline molecular sieve, which are characterized as being shape-selective. Removal of such debris also generally improves traffic entering and exiting crystallite pores, allowing reaction products to escape prior to undergoing subsequent degradation.

Overall, therefore, the post-synthesis acid treatment of the molecular sieve used in the present invention is likely to remove amorphous silicon aluminum phosphate acid, silicophosporous acids, and/or phosphoric acids (all of which are undesired acid catalysts), while in the process increase the accessibility of the crystallite pores of the molecular sieve to olefin feeds and products. Thus, a greater amount of shape-selective acid sites residing with the molecular sieve pores is available for reaction. This explanation therefore accounts for not only the observed increase in product selectivity, but also in catalyst activity, resulting from the acid treatment. Additionally, the acid washing can even remove non-selective acid sites from the external surface of the molecular sieve crystallites themselves. As evidence of this, x-ray photoelectron spectroscopy X(PS) measurements of both non acid-washed and acid-washed SAPO-11 molecular sieve crystallites show a decrease, as a result of acid washing, in surface concentrations of silicon and aluminum with a corresponding increase in phosphorous.

In considering changes, resulting from the acid wash, in acid properties of SAPO molecular sieves in particular, it should be noted that pure aluminum phosphate is a non-acidic material. However, the replacement of phosphorous (+5 oxidation state) with silicon (+4 oxidation state), to form a SAPO material necessarily involves the addition of acidic protons to balance the charge offset. Thus, the observed removal of surface silicon due to acid washing is consistent with the hypothesis that external acidity is reduced, leading to even greater shape selectivity. If a SAPO molecular sieve is employed, therefore, a significant property resulting from acid washing is the difference in composition between the outer surface and bulk framework structure of the material. This difference may be conveniently characterized according to the relative contributions of external and internal phosphorous, where the former can be determined experimentally (e.g. by XPS) and that latter may be either measured or deduced from the molecular sieve empirical formula. For un-washed molecular sieves, the surface and bulk phosphorous content (measured as a mole fraction) should be identical, so that the phosphorous "surface/bulk ratio" is 1. In contrast, preferred acid-washed SAPO molecular sieves of the present invention preferably have a phosphorous surface/bulk ratio of greater than about 1.3 and more preferably greater than about 1.5.

The acid-washed molecular sieve is preferably incorporated into solid catalyst particles where the molecular sieve is present in an amount effective to promote the desired conversion of light olefins to heavier olefin products. Thus, these solid particles comprise a catalytically effective amount of the molecular sieve and either an inorganic oxide binder, a filler, or both to provide a desired level of mechanical strength or attrition resistance of the bound catalyst.

The total amount of binder and filler material preferably contributes from about 20% to about 80% of the total catalyst weight. In addition to enhancing the catalyst strength properties, the binder and/or filler materials allow the molecular sieve crystallite powder to be bound into larger particle sizes suitable for commercial catalytic processes. The molecular sieve/binder composite may be formed into a wide variety of shapes including, for example, extrudates, spheres, pills, and the like. The binder and/or filler material is often, to some extent, porous in nature and may or may not be effective to promote the desired oligomerization of light olefins through, for example, the provision of acid sites. The binder and filler materials may also promote conversion of the feed stream and often provide reduced selectivity to the desired product or products relative to the catalyst.

Examples of preferred binder materials include, but are not limited to, alumina, silica, aluminum phosphate, silica-alumina, zirconia, titania, and mixtures thereof. Filler materials can include, for example, synthetic and naturally occurring substances such as clays, metal oxides, silicas, aluminas, silica-aluminas, and mixtures thereof. In referring to the types of binders and fillers that may be used, it should be noted that the term silica-alumina does not mean a physical mixture of silica and alumina but means an acidic and amorphous material that has been cogelled or coprecipitated. This term is well known in the art and is described, for example, in U.S. Pat. Nos. 3,909,450; 3,274,124; and 4,988,659. In this respect, it is possible to form other cogelled or coprecipitated amorphous materials that will also be effective as either binder or filler materials. These include silica-magnesias, silica-zirconias, silica-thorias, silica-berylias, silica-titanias, silica-alumina-thorias, silica-alumina-zirconias, aluminophosphates, mixtures of these, and the like. Preferably, the filler is a clay, since clays are known to be essentially inert under a wide range of reaction conditions. Suitable clays include commercially available products such as kaolin, kaolinite, montmorillonite, saponite, and bentonite. These clays can be used as mined in their natural state, or they may also be employed in highly active forms, typically activated by an acid treatment procedure. Commercial suppliers of these clays include Thiele Kaolin Company (Sandersville, Ga.), American Colloidal Co. (Arlington Heights, Ill.,), GSA Resources, Inc. (Tucson, Ariz.), Albion Kaolin Co. (Hephzibah, Ga.), and others.

In preparing a bound catalyst of the present invention, a slurry of the acid-washed crystalline molecular sieve powder, the inorganic oxide binder, and the filler (if used) is formed. The slurry will contain an appropriate sol, or carrier material, of the inorganic oxide binder used for suspending the molecular sieve. In the case of incorporating alumina, silica, magnesia, zirconia, or titania binders into the bound catalyst composition of the present invention, it is appropriate to use a hydrosol. For example, any of the transitional aluminas can be mixed with water and an acid to give an aluminum sol. Acids for this application may include inorganic acids such as nitric, hydrochloric, and sulfuric, or organic acids, especially carboxylic acids such as formic, acetic, propionic, and the like. Alternatively, an aluminum sol can be made by for example, dissolving aluminum metal in hydrochloric acid and then mixing the aluminum sol with the alumina powder. When an alumina binder is desired, it is also possible to use a solution of boehmite, which may be available from commercial sources (e.g. Versal™, available from UOP, LLC, Des Plaines, Ill.) or aluminum nitrate in place of the aluminum sol.

Types of silica sols used to form a bound catalyst for use in the oligomerization process are commercially available as aquasols or organosols (e.g. Cab-O-Sil™, available from Cabot Corp., Boston, Mass. or HiSil™, available from PPG Industries, Inc., Pittsburgh, Pa.) containing dispersed colloidal silica particles. Sodium silicate can also be used as a silica sol and combined with an acidic aluminum sol to ultimately yield a silica-alumina binder in the final catalyst. Otherwise, a silica gel, such as commercially available Ludox™ (Aldrich Chemical Co., Milwaukee, Wis.) may also be used to provide a silica binder in the molecular sieve catalyst. Silicic acid is another possible source of silica. If a magnesia binder is desired, the starting slurry will contain hydrolyzed magnesium alkoxide. When a zirconia binder is used for the catalyst preparation, the preferred starting acidic sol is an aqueous zirconium acetate solution, which is preferably combined with a urea gelling agent. When a titania binder is used, the acidic sol is preferably a solution of titanyl oxychloride, which is also preferably combined with a urea gelling agent. Acidic colloidal suspensions of various inorganic oxides are also available from commercial suppliers such as Nano Technologies, Inc. (Ashland, Mass.). The amount of sol added to the slurry is based on the desired amount of binder in the finished catalyst. Those skilled in the art will readily appreciate the relationship between the molecular sieve:sol weight ratio of the slurry and the resulting molecular sieve:binder ratio in the catalyst.

As discussed, the acid-washed molecular sieve-containing catalyst may also incorporate a filler in addition to an inorganic oxide binder. The filler may itself be an inorganic oxide (e.g. alumina) that is added into the synthesis slurry in a powdered form rather than a sol. Preferably, the filler is a clay selected from the group of suitable clays provided previously. In some cases, the addition of a clay filler may improve the overall strength of the bound catalyst, where this improvement is measured by the amount of finished catalyst material lost during a standard attrition test (i.e. attrition loss). Loss of the catalyst by attrition can be measured by fluidizing the catalyst in air for a given period of time, collecting and weighing the fines generated, and then calculating an attrition loss as an average percent of the initial catalyst weight per hour.

It is also within the scope of the present invention to include other components in the slurry that may have an impact on the final catalyst properties. For example, International Publication WO 99/21653 discloses the use of an external phosphorous source, which may have a favorable impact on the catalyst and process of the present invention. The teachings of this reference relating to potential sources of phosphorous and relative amounts desired in the catalyst composition are hereby incorporated by reference.

Depending on the average particle size of agglomerated molecular sieve crystallites present in the slurry, it may be desired to mill the slurry in order to break these agglomerates apart, thereby reducing the agglomerate particle size and/or giving a narrower particle size distribution. Milling can be done by means known in the art such as ball milling for times from about 30 minutes to about 5 hours and preferably from about 1.5 to about 3 hours. It is believed that using a slurry with a particle size distribution that has been adjusted in this manner improves the structural characteristics of the bound molecular sieve catalyst. Care must be taken, however, not to mill the slurry so extensively as to destroy the crystallite structure of the molecular sieve.

It should also be noted that, in addition to the molecular sieve powder, sol of the inorganic oxide binder, and filler (if used), the slurry will often contain water. The amount of water is often adjusted after any milling operation in order to obtain a viscosity of the milled slurry in the range from about 30 to about 600 centipoise. Prior to drying, it is generally preferred that the slurry components are well mixed to ensure a uniform slurry composition. A period of high shear mixing of about 15 minutes, for example, is effective in most cases for obtaining the proper uniformity. It is important to initiate the subsequent drying step prior to the onset of gelling of the slurry, usually about 1 hour after mixing.

The well-mixed slurry, either with or without prior milling, is then dried at a temperature from about 50° C. to about 300° C. for a time from about 1 to about 24 hours to form dried, shaped particles. These particles may or may not be subsequently milled or otherwise reduced in size at this point to provide catalyst physical properties that in turn lead to the ultimately desired pressure drop characteristics, fluidization velocity, diffusion resistance, and other properties. The dried, shaped particles have an average effective diameter generally from about 1 to about 10 millimeters, although considerably smaller catalyst particles could be used if a fluidized bed process is employed. By effective diameter is meant, for non-spherical shapes, the diameter that the shaped particle would have if it were molded into a sphere. In a preferred embodiment, the dried, shaped particles are substantially cylindrical in shape (i.e. extrudates).

Finally, the dried, shaped catalyst particles are calcined at a temperature from about 400° C. to about 900° C. in an air environment for a time from about 1 to about 10 hours to effectively set the inorganic oxide binder. The calcination step also removes any remaining template material that may be present within the crystalline molecular sieve. In some cases, the catalyst may be activated in a modified calcination step wherein the organic template is first decomposed in a flow of pure nitrogen. The oxygen concentration is then gradually increased to combust any residual hydrocarbons in the molecular sieve. It is also possible to combine the drying and calcining operations into a single step.

The oligomerization of light olefins is effected by contacting the light olefin feed with the acid-washed molecular sieve-containing catalyst at oligomerization conditions, thereby forming the desired heavier olefin products. As mentioned, the feed can be either in the liquid or vapor phase with the liquid phase being preferred. Contacting the light olefin with the acid-washed molecular sieve catalyst can be done in a continuous mode or a batch mode with a continuous mode being preferred. The amount of time that the light olefin is in contact with the acid-washed molecular sieve catalyst must be sufficient to oligomerize the feed to the proper extent or average degree of polymerization. When the process is carried out in a batch process, the contact time varies from about 0.001 to about hours and preferably from about 0.01 to about 1.0 hour. The longer contact times are used at lower temperatures while shorter times are used at higher temperatures, assuming all other process variables are equal. Further, when the process is carried out in a continuous mode, the weight hourly space velocity (WHSV) based on the total feed (including any diluents) can vary from about 0.1 hr$^{-1}$ to about 20 hr$^{-1}$ and preferably from about 0.5 hr$^{-1}$ to about 10 hr$^{-1}$. As is understood in the art, the weight hourly space velocity is the weight flow of the feed divided by the catalyst weight. This term provides a measure of how many equivalent weights of the catalyst inventory are processed every hour as methanol. Generally, the process must be carried out at elevated temperatures in order to form light olefins at a fast enough rate. Thus, the process is preferably carried out at a temperature from about 40° C. to about 250° C. The process may be carried out over a wide range of pressure including autogenous pressure. Preferably, therefore, the oligomerization conditions include an absolute pressure from about 0.5 to about 100 atmospheres (about 7.4 to about 1500 psig).

Optionally, the light olefin feed may be diluted with an inert or slightly reactive diluent in order to more efficiently oligomerize the olefin while reducing the production of undesired side products. Examples of the diluents which may be used are paraffinic hydrocarbons such as propane, butane, pentane, hexane, heptane, octane, nonane, decane, etc., or gaseous components such as helium, argon, nitrogen, carbon monoxide, carbon dioxide, hydrogen, and steam. The amount of diluent used can vary considerably and usually represents from about 5 to about 90 weight percent of the feedstock and preferably from about 25 to about 75 weight percent.

The actual configuration of the oligomerization reaction zone may be any well-known catalyst reaction apparatus known in the art. Thus, a single reaction zone or a number of zones arrange d in series or parallel may be used. When multiple reaction zones are used, one or more molecular sieve catalysts may be used in series to produce the desired product mixture In addition to a fixed bed, a dynamic bed system, e.g., fluidized or moving, may be used. Such a dynamic system would facilitate any regeneration of the acid-washed molecular sieve catalyst that may be required. If regeneration is required, the catalyst can be continuously introduced as a moving bed to a regeneration zone where it can be regenerated by means such as oxidation in an oxygen-containing atmosphere to remove carbonaceous materials.

The following examples are presented in illustration of this invention and are not intended as undue limitations on the generally broad scope of the invention as set forth in the appended claims.

EXAMPLE 1

SAPO-11 molecular sieve was prepared according to the prior art as taught in U.S. Pat. No. 4,440,871. A reaction mixture was prepared by combining 85% orthophosphoric acid with distilled water, then adding a precipitated pseudo-boehmite form of alumina as Versal™ 250 and mixing) until homogeneous. Silica as HiSil™ 250 and di-n-propylamine were added and blended into provide a reaction mixture composition in molar oxide ratios of:

1.8 Pr$_2$NH: Al$_2$O$_3$: P$_2$O$_5$: 0.2 SiO$_2$: 50 H$_2$O

An amount of SAPO-11 corresponding to 2 mass-% of the Al and P oxides in the reaction mixture was added as seed and mixed until homogeneous. The reaction mixture was heated with stirring for 12 hours at 195° C. at autogenous pressure, then cooled to ambient temperature to form a SAPO product slurry. SAPO crystallite product was recovered and washed by centrifugation, dried, and calcined at 650° C. The recovered SAPO-11 was designated as Molecular Sieve R. or the reference molecular sieve.

EXAMPLE 2

Acid-washed SAPO-11 molecular sieve of the invention was prepared by acid washing the reference Molecular Sieve R from Example 1. For each 100 grams of SAPO-11, 400 cc of distilled water was added. HNO$_3$ solution in a concentration of 17.7 mass-% was added to obtain a pH of about 2. The acidic solution was continually added to the slurry of the SAPO powder and water to maintain pH of 2 for about 18 hours. The acid-washed SAPO-11 was filtered, washed repeatedly with distilled water until the wash water showed a neutral pH and dried at 110° C. The sample was designated Molecular Sieve A. The surface composition (in mole-%)of Molecular Sieve A was measured using x-ray photoelecton spectroscopy (XPS), for comparison with that of Molecular Sieve R:

| Molecular Sieve | % Al | % Si | % P | surface/bulk ratio |
|---|---|---|---|---|
| R (SAPO-11) | 66.8 | 9.7 | 23.5 | |
| A | 57.1 | 5.8 | 37.1 | 1.58 |

The accompanying x-ray photoelectron spectroscopy measurements (XPS) show a decrease, upon acid washing, in surface concentrations of silicon and aluminum and an increase in surface concentration of phosphorous. The change in phosphorous is the basis for determining the "surface/bulk ratio" characteristic of acid washed SAPO materials, as defined previously. As demonstrated by the above example, this value is >1.5 due to the acid wash employed for Molecular Sieve A. The changes in surface characteristics are, in fact, consistent with the hypothesis that external acidity is removed.

EXAMPLE 3

The acid-washed Molecular Sieve A and the standard (un-washed) SAPO-11 crystallites (Molecular Sieve R) were bound according to the procedures described previously to provide extrudates, or cylindrically-shaped catalyst particles having a diameter of about 1–2 mm. The binder used was silica and contributed to 35% of the total finished catalyst weight. The catalysts made using Molecular Sieve R and Molecular Sieve A were designated, respectively, Catalyst R and Catalyst A.

Samples of Catalyst R and Catalyst A were tested in a pilot plant to compare their performance in terms of light olefin oligomerization activity and selectivity. The experiment was performed using oligomerization conditions within the preferred commercial operating ranges as defined previously; namely, a pressure of about 900 psig (61 atmospheres, gauged and a maximum catalyst bed temperature of 218° C. were used in each case. The feed was a blend of 50/50 propylene/propane by weight. Since the catalysts R and A exhibited different oligomerization activity, the catalyst WHSV was adjusted to achieve 80% propylene conversion for each test. The olefin product slate obtained using the two catalyst samples, and measured at the reactor effluent using gas chromatography (GC) is provided below:

Feed: 50/50 w/w Propylene/Propane
Maximum Catalyst Temperatures: 218° C.
Pressure: 900 psig
Propylene Conversion: 80%

| Product Selectivity, wt-% | Catalyst R (Reference) | Catalyst A (Acid washed SAPO-11) |
|---|---|---|
| hexene (dimer) | 12 | 32 |
| nonene (trimer) | 37 | 48 |
| dodecene (tetramer) | 23 | 5 |
| others | 28 | 15 |

These results show the improvement in selectivity to the valuable hexene and nonene dimer and trimer products using the acid-washed molecular sieve catalyst, compared to the reference. Industrially, hexene is valued for its use in co-monomer applications, whereas nonene is important for its use as a plasticizer intermediate. The yield enhancement of both of these products, therefore, carries very important commercial implications.

EXAMPLE 4

Catalyst A was tested under conditions identical to those used in Example 3, except that the WHSV was reduced to provide an increase in propylene conversion from 80% to 95% The GC results are summarized below and compared to those obtained for the same catalyst in Example 3:

Feed: 50/50 w/w Propylene/Propane
Maximum Catalyst Temperature: 218° C.
Pressure: 900 psig
Catalyst: Catalyst A (acid-washed, bound 65% SAPO-11)

| Product Selectivity, wt-% | 80% Propylene Conversion | 95% Propylene Conversion |
|---|---|---|
| hexene (dimer) | 32 | 42 |
| nonene (trimer) | 48 | 35 |
| dodecene (tetramer) | 5 | 5 |
| others | 15 | 18 |

Thus, at the higher conversion the dimer selectivity actually increased using the acid-washed SAPO-11. This observation is totally unexpected and cannot be explained by historic oligomerization mechanisms that do not include shape selective catalysis. Such mechanisms predict the higher oligomers such as trimers and tetramers being directionally favored at higher conversions, since oligomerization is a sequential process of monomer additions to growing chains.

EXAMPLE 5

Catalysts R and A were tested again under the conditions described in Example 3, except that, in both cases, the identical process conditions were used in order to more directly examine the effect of acid washing the molecular sieve component of the catalyst. The oligomerization was performed again using a feed stock of 50/50 propylene/propane by weight, a maximum catalyst bed temperature of 218° C., and a reaction pressure of 90° C. psig. In this experiment, however, the same feed WHSV of 1.1 hr$^{-1}$ was used for testing both the acid-washed (Catalyst R) and un-washed (Catalyst A) molecular sieve catalysts. The G.C. results, showing the $C_3$, $C_6$, and $C_7$ olefin product distribution, as well as the breakdown of the $C_7$ olefin isomers, are given below:

Feed: 50/50 w/w Propylene/Propane
Maximum Catalyst Temperature: 218° C.
Pressure: 900 psig
WHSV: 1.1 hr$^{-1}$

|  | Catalyst R (Reference) | Catalyst A (Acid-washed SAPO-11) |
|---|---|---|
| Propylene Conversion, % | 81 | 90 |
| Product Selectivity, wt % | | |
| hexene (dimer) | 14.4 | 37.9 |
| nonene (trimer) | 40.3 | 38.9 |
| dodecene (tetramer) | 19.4 | 4.1 |
| heptene | 4.0 | 5.7 |
| others | 21.9 | 13.4 |
| Heptene Isomers, wt % | | |
| n—$C_7$ | 1.2 | 3.1 |
| Methyl $C_6$ | 29.7 | 52.2 |
| Dimethyl $C_5$ | 68.9 | 44.3 |
| Trimethyl $C_4$ | 0.2 | 0.4 |

These results further show the benefits of acid washing the molecular sieve used for the oligomerization catalyst. Under identical reaction conditions, the acid washed molecular sieve catalyst demonstrated not only a higher conversion, but also a shifting of the product slate toward the lower molecular weight oligomers. Thus, a significantly greater amount of hexene was produced, coupled with a large decrease in byproduct make. Furthermore, considering the composition of the $C_7$ olefin product, which accounted for 4–6% by weight of the converted propylene, the heptenes resulting from the use of the acid washed SAPO-11 were considerably less branched than those produced with the unwashed catalyst. The increase in linearity (i.e. the reduction in branching) achieved using the acid washing procedure of the present invention is evident from the higher makes of n-heptene and methyl-hexene with a corresponding reduction in the amount of poly-methyl olefins produced. It is known that a decrease in the branching degree of this material benefits its ability to undergo downstream hydroformylation for plasticizer production.

EXAMPLE 6

Catalyst A was tested in a plant with a feed containing a major amount of isobutylene. Specifically, the feed was composed of 0.6 wt-% propylene, 1.9 wt-% propane, 0.6 wt-% butene-1, 25.0 wt-% isobutylene, 33.1 wt-% isobutane, 1.3 wt-% normal butane, and 37.5 wt-% isooctane.

Very high isobutylene conversions were possible even at elevated feed space velocities. Furthermore, exceptional isobutylene timer selectivities were noted, significantly higher than those expected from conventional acid catalysts such as phosphoric acid. For instance, at a WHSV of 5.6 hr$^{-1}$, a catalyst bed maximum temperature of 194° C., and a plant pressure of 900 psig, the following results were obtained:

| isobutylene conversion, % | 95.4 |
|---|---|
| octene selectivity, wt % | 62.2 |
| dodecene selectivity, wt % | 36.0 |

Within the octene fraction, 99.0% was highly-branched trimethylpentenes, with, therefore, very little dimethylhexanes. Within the trimethylpentene fraction 84% of the isomers had the 2,2,4 trimethylpentene backbone, 12% of them had the 2,3,4 backbone, and the remainder had the 2,2,3 and 2,3,3 backbones.

At the even higher WHSV of 14.5 hr$^{-1}$ with catalyst bed maximum temperature of e215° C. and a plant pressure of 900 psig, the results were as follows:

| | |
|---|---|
| isobutylene conversion, % | 88.6 |
| octene selectivity, wt % | 71.2 |
| dodecene selectivity, wt % | 27.6 |

Under these conditions, within the octene fraction of the product, 99.1% was highly-branched trimethylpentenes. Within the trimethylpentene fraction 86% had the 2,2,4 trimethylpentane backbone, 11% had the 2,3,4 backbone, and the remainder had the 2,2,3 and 2,3,3 backbones.

At the high WHSV of 5.6 hr$^{-1}$, but at a much lower plant pressure of 300 psig and with a feed having double the isooctane as in the previous cases (and correspondingly lower levels of all other components), only a moderate reduction in isobutylene conversion was observed (compared to the example above using a WHSV of 5.6 hr$^{-1}$). The results in this case were:

| | |
|---|---|
| isobutylene conversion, % | 87.4 |
| octene selectivity, wt % | 78.6 |
| dodecene selectivity, wt % | 20.8 |

Within the octene fraction of the product, 98.9% was trimethylpentenes. Within the trimethylpentene fraction, 87.6% of the isomers had the 2,2,4 trimethylpentane backbone, 8.9% had the 2,3,4 backbone and the rest had the 2,2,3 and 2,3,4 backbones.

An extraordinary space velocity and an isooctane-free feed (feed composition: 0.96 wt-% propylene, 3.03 wt-% propane, 0.96 wt-% 1-butene, 40.0 wt-% isobutene, 52.98 wt-% isobutane, and 2.07 wt-% normal butane) did substantially reduce the isobutylene conversion. For instance, at a WHSV of 14.7 hr$^{-1}$, a 203° C. catalyst bed maximum temperature, and 300 psig plant pressure, the following results were obtained:

| | |
|---|---|
| isobutylene conversion, % | 55.0 |
| octene selectivity, wt % | 66.0 |
| dodecene selectivity, wt % | 32.1 |

Acid-washed SAPO-11, prepared according to the present invention, was therefore not only higher active for the oligomerization of isobutylene, but also very selective for the dimer and trimer oligomers. Furthermore, the catalyst of this example, using an acid-washed molecular sieve, performed well with a solvent such as isooctane, which maintained the reactor contents in a substantially liquid state.

What is claimed is:

1. A process for oligomerizing an olefinic feed, the process comprising:

a) providing a catalyst comprising a crystalline silicon aluminophosphate molecular sieve characterized by a 3-dimensional framework structure type of SAPO-11 or SAPO-41 and having a chemical composition on an anhydrous basis expressed by an empirical formula of:

where "x" is the mole fraction of Si and has a value of at least 0.005; "y" is the mole fraction of Al and has a value of at least 0.01; "z" is the mole fraction of P and has a value from greater than 0 to about 0.6; the molecular sieve having been washed at washing conditions with a strong acid having a pK$_a$ of less than 2.0, and;

b) contacting the light olefin feed with the catalyst at oligomerization conditions to yield a higher olefin product.

2. The process of claim 1 where the molecular sieve has a phosphorous surface/bulk ratio of greater than 1.3.

3. By The process of claim 2 where the silicon aluminophosphate has the crystal structure of SAPO-11.

4. The process of claim 1 where the catalyst further comprises a binder selected from the group consisting of alumina, silica, aluminum phosphate, silica alumina, zirconia, titania, and mixtures thereof.

5. The process of claim 1 where the light olefin feed comprises propylene.

6. The process of claim 5 where the higher olefin product comprises hexene present in an amount of at least 30% by weight, relative to the light olefin feed weight.

7. The process of claim 5 where the higher olefin product comprises a C$_7$ olefin product containing linear heptene and methyl hexenes present in an amount of at least 40% by weight, relative to the C$_7$ olefin product weight.

8. The process of claim 1 where the oligomerization conditions comprise a temperature from about 40° C. to about 250° C., an absolute pressure from about 0.5 to about 100 atmospheres, and a feed WHSV from about 0.1 to about 20 hr$^{-1}$.

9. The process of claim 1 where the acid is an aqueous solution selected from the group consisting of aqueous HNO$_3$, HCl, H$_2$SO$_4$, HBr, HI, and mixtures thereof.

10. The process of claim 1 where the aqueous solution has a pH from about 1 to about 4.

11. The process of claim 1 where the washing conditions comprise a temperature from about 0° C. to about 100° C. and a residence time from about 0.5 to about 48 hours.

12. A process for oligomerizing a light olefin feed to a higher olefin product, the process comprising contacting the feed at oligomerization conditions with a catalyst having been treated with a strong acid having a pK$_a$ of less than about 5.0, the catalyst comprising a crystalline silicon aluminophosphate molecular sieve characterized by a 3-dimensional framework structure type of SAPO-11 or SAPO-41 and having a chemical composition on an anhydrous basis expressed by an empirical formula of:

where "x" is the mole fraction of Si and has a value of at least 0.005; "y" is the mole fraction of Al and has a value of at least 0.01; "z" is the mole fraction of P and has a value from greater than 0 to about 0.6.

* * * * *